(12) United States Patent
Goshen (10) Patent No.: US 10,147,168 B2
(45) Date of Patent: Dec. 4, 2018

(54) SPECTRAL CT

(71) Applicant: KONINKLIJKE PHILIPS N.V., Eindhoven (NL)

(72) Inventor: Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 114 days.

(21) Appl. No.: 15/369,943

(22) Filed: Dec. 6, 2016

(65) Prior Publication Data

US 2017/0124686 A1 May 4, 2017

Related U.S. Application Data

(62) Division of application No. 14/232,292, filed as application No. PCT/IB2012/053520 on Jul. 10, 2012, now Pat. No. 9,547,889.

(Continued)

(51) Int. Cl.
*G06T 5/00* (2006.01)
*A61B 6/03* (2006.01)
*A61B 6/00* (2006.01)

(52) U.S. Cl.
CPC .............. *G06T 5/002* (2013.01); *A61B 6/032* (2013.01); *A61B 6/481* (2013.01); *A61B 6/482* (2013.01);

(Continued)

(58) Field of Classification Search
CPC ................. G06T 7/0012; G06T 11/003; G06T 2207/10081; G06T 7/0081; A61B 6/0306
See application file for complete search history.

(56) References Cited

U.S. PATENT DOCUMENTS 6,704,437 B1 3/2004 He
6,754,298 B2 6/2004 Fessler
(Continued)

FOREIGN PATENT DOCUMENTS

| JP | 2008246022 | 10/2008 |
|---|---|---|
| JP | 2013212024 | 10/2013 |
| WO | 2011064683 | 6/2011 |

OTHER PUBLICATIONS

Barrett, et al., "Preventing Nephropathy Induced by Contrast Medium", 2006, New England Journal of Medicine.
(Continued)

*Primary Examiner* — Mia M Thomas (57) ABSTRACT

Aspects include estimating structure models for a voxel(s) of a spectral image. The estimation is based on a noise model. Aspects further include fitting structure models to a 3D neighborhood about the voxel(s), selecting one of the structure models for the voxel(s) which is based on the fittings and predetermined model selection criteria. Aspects further include de-noising the voxel(s) based on the selected structure model, which produces a set of de-noised spectral images. Other aspects include generating a virtual contrast enhanced intermediate image for each energy image of a set of spectral images. The energies correspond to different energy ranges which are based on de-noised spectral images, decomposed de-noised spectral images, an iodine map, and a contrast enhancement factor. Aspects further include generating final virtual contrast enhanced images. The final virtual contrast enhanced images are generated by incorporating a simulated partial volume effect with the intermediate virtual contrast enhanced images.

20 Claims, 7 Drawing Sheets

Related U.S. Application Data (60) Provisional application No. 61/508,178, filed on Jul. 15, 2011.

(52) U.S. Cl.
CPC .......... *A61B 6/5205* (2013.01); *A61B 6/5258* (2013.01); *G06T 2200/04* (2013.01); *G06T 2207/10072* (2013.01); *G06T 2207/10081* (2013.01); *G06T 2207/30004* (2013.01); *G06T 2207/30008* (2013.01)

(56) References Cited

U.S. PATENT DOCUMENTS

| | | | |
|---|---|---|---|
| 7,533,000 B2 * | 5/2009 | Statham | G01J 3/28 250/306 |
| 7,561,727 B2 * | 7/2009 | Conrad-Hansen | G06T 7/0012 378/28 |
| 7,734,076 B2 | 6/2010 | Du | |
| 7,844,090 B2 * | 11/2010 | De Bruijne | G06T 7/0012 378/46 |
| 7,867,998 B2 | 1/2011 | Kim | |
| 7,903,860 B2 * | 3/2011 | Grasruck | G06T 5/50 382/132 |
| 7,970,196 B2 * | 6/2011 | Arnold | G06T 7/0012 378/4 |
| 7,982,747 B1 | 7/2011 | Dulaney | |
| 8,594,770 B2 | 11/2013 | Wood | |
| 8,630,467 B2 * | 1/2014 | Masumoto | G06F 19/321 382/128 |
| 8,885,968 B2 * | 11/2014 | Honda | H03K 5/1252 382/260 |
| 9,330,443 B1 * | 5/2016 | Zou | G06T 5/002 |
| 2004/0252870 A1 | 12/2004 | Reeves | |
| 2006/0013460 A1 * | 1/2006 | Dehmeshki | G06T 7/0012 382/131 |
| 2006/0097176 A1 | 5/2006 | Szu | |
| 2006/0103892 A1 | 5/2006 | Schulze | |
| 2006/0280350 A1 * | 12/2006 | Conrad-Hansen | G06T 7/0012 382/128 |
| 2007/0016073 A1 | 1/2007 | Kim | |
| 2008/0063135 A1 | 3/2008 | DeMan | |
| 2008/0247618 A1 | 10/2008 | Laine | |
| 2008/0292194 A1 | 11/2008 | Schmidt | |
| 2009/0052612 A1 * | 2/2009 | Wu | A61B 6/032 378/5 |
| 2009/0117559 A1 * | 5/2009 | Liaw | C12Q 1/6883 435/6.14 |
| 2009/0135998 A1 * | 5/2009 | Rossl | G06T 5/50 378/98 |
| 2009/0161939 A1 * | 6/2009 | Wu | G06T 7/0012 382/132 |
| 2009/0216094 A1 * | 8/2009 | De Bruijne | G06T 7/0012 600/309 |
| 2009/0285480 A1 | 11/2009 | Bennett | |
| 2010/0128844 A1 | 5/2010 | Thomsen | |
| 2010/0166277 A1 | 7/2010 | Raupach | |
| 2010/0328313 A1 | 12/2010 | Zamyatin | |
| 2011/0064292 A1 | 3/2011 | Chen | |
| 2011/0150307 A1 | 6/2011 | Souza | |
| 2011/0188715 A1 | 8/2011 | Shotton | |
| 2011/0286651 A1 | 11/2011 | Yu | |
| 2011/0292400 A1 * | 12/2011 | Fleming | A61B 5/0066 356/479 |
| 2012/0039518 A1 | 2/2012 | Bruder | |
| 2012/0069170 A1 | 3/2012 | Gesley | |
| 2012/0087565 A1 * | 4/2012 | Garud | G06T 5/002 382/132 |
| 2012/0148123 A1 | 6/2012 | Gindele | |
| 2012/0224760 A1 * | 9/2012 | Goshen | G06T 5/002 382/131 |
| 2012/0263360 A1 | 10/2012 | Zhu | |
| 2013/0094749 A1 * | 4/2013 | Oh | A61B 6/503 382/133 |
| 2013/0128123 A1 | 5/2013 | Rifkah | |
| 2013/0243348 A1 | 9/2013 | Goshen | |
| 2013/0294669 A1 | 11/2013 | El-Baz | |
| 2013/0329851 A1 | 12/2013 | Rossl | |
| 2014/0035943 A1 * | 2/2014 | Statham | G06T 11/001 345/593 |
| 2014/0056503 A1 | 2/2014 | Schecter | |
| 2014/0126685 A1 * | 5/2014 | Deuerling-Zheng | A61B 6/4441 378/4 |
| 2014/0133729 A1 * | 5/2014 | Goshen | G06T 5/002 382/131 |
| 2014/0193061 A1 | 7/2014 | Miller | |
| 2015/0248782 A1 | 9/2015 | Proksa | |
| 2015/0254843 A1 | 9/2015 | Brown | |
| 2016/0171648 A1 | 6/2016 | Thibault | |
| 2016/0321803 A1 * | 11/2016 | Lamash | G06T 7/0012 |
| 2018/0025515 A1 * | 1/2018 | Shechter | G06T 11/008 382/131 |

OTHER PUBLICATIONS

Goshen, et al., "An iodine-calcium separation analysis and virtually non-contrasted image generation obtained with single source dual energy MDCT" 2008, IEEE Trans. on Nuclear Sciene.

Teague, et al., "Potential clinical and economic benefits of low-contrast-dose CT angiography" 2009; Applied Radiology.

Tepel, et al., "Contrast-Induced Nephropathy: A Clinical Evidence-Based Approach", 2006, Circulation.

Wunderlich, et al., "Image Covariance and Lesion Detectability in Direct Fan-Beam X-ray Computed Tomography", 2006, Phys. Med. Biol.

* cited by examiner

SPECTRAL CT

CROSS REFERENCE TO RELATED APPLICATIONS

This application is a divisional application of U.S. application Ser. No. 14/232,292, which is a national filing of PCT application Ser. No. PCT/IB2012/053520, filed Jul. 10, 2012, published as WO 2013/011418 A2 on Jan. 24, 2013, which claims the benefit of U.S. provisional application Ser. No. 61/508,178 filed Jul. 15, 2011, which is incorporated herein by reference.

FIELD OF THE INVENTION

The following generally relates to computed tomography (CT) and more particularly to spectral CT.

BACKGROUND OF THE INVENTION

A CT scanner generally includes an x-ray tube that emits ionizing radiation that traverses an examination region and a portion of an object or subject therein and illuminates a detector array disposed across the examination region, opposite the x-ray tube. The detector produces projection data indicative of the detected radiation. The data can be reconstructed to generate volumetric image data indicative of the portion of the object or subject. With spectral CT, the projection data includes signals which are acquired concurrently and that correspond to different photon energy ranges. There are several approaches for performing spectral CT. For example, the CT scanner may include two or more sources, at least one source configured to switch between at least two different kVps, and/or a detector array with energy-resolving detectors.

With spectral CT, two acquired signals can be used to determine the photoelectric and Compton contributions of each signal and identify an unknown material by its value of photoelectric and Compton contribution. Generally, because any two linearly independent sums of two basis functions span the entire attenuation coefficient space, any material can be represented by a linear combination of two basis materials. This works especially well in materials, such as iodine, that have a k-edge energy close to the mean value of a diagnostic energy range. Furthermore, the additional spectral information improves the quantitative information that can be determined about the scanned object and its material composition. The basis material also allows for generating a monochromatic image, a material cancellation image, an effective atomic number image, and electron density image.

Again, CT scanners emit ionizing radiation. Unfortunately, ionizing radiation may damage or kill cells and/or increase the risk of cancer. The literature has indicated that dose levels from CT typically exceed those from conventional radiography and fluoroscopy. However, the radiation dose for a particular imaging procedure cannot just be lowered as a lower dose leads to increased image noise and thus blurrier or un-sharp image. Moreover, spectral CT images are already inherently noisier than conventional non-spectral images. For example, in a dual energy study, each image is based on roughly half of the radiation dose of a corresponding non-spectral conventional scan. Furthermore, the estimate of the material decomposition is based on projections between two vectors with a narrow angle there between. The combination of these two factors, i.e., large noise and narrow angle, amplifies significantly the noise in the estimated material decomposition.

Contrast enhanced CT studies capture the transit of an administered radio-contrast material through vascular tissue. Generally, for contrast enhanced CT, a bolus of a radio-contrast material is intravenously administered to a patient, and a region of interest of the patient that includes the vascular tissue of interest is scanned. The radio-contrast material causes the x-ray density in the vascular tissue of interest to temporarily increase as the radio-contrast material flows through the vascular tissue, resulting in enhanced data. However, after administration of a contrast material, some patients experience idiosyncratic effects and certain patients may experience severe and potentially life-threatening allergic reactions. Contrast material may also induce kidney damage, and some patients have developed an acute deterioration of their kidney function. Generally, a larger contrast material volume results in higher contrast to noise (CNR) images, while a lower volume leads to lower CNR image. Unfortunately, as the contrast material volume increases, so does its associated risks.

SUMMARY OF THE INVENTION

Aspects of the present application address the above-referenced matters and others.

According to one aspect, a method includes estimating a local noise value for one or more voxels of a spectral image of a set of spectral images corresponding to different energy ranges, producing a noise model for the image, estimating local structure models for a voxel of the spectral image based on a corresponding noise model, fitting a set of the local structure models to a three dimensional neighborhood of voxels in the image about a voxel in the image, selecting one of the local structure models for the voxel based on the fittings and predetermined model selection criteria, and de-noising the voxel based on the selected local structure model by replacing a value of the voxel with a value estimated based on the selected local structure model, wherein a plurality of the voxels of a plurality of spectral images in the set of spectral images are de-noised, producing a set of de-noised spectral images.

In another aspect, a computing apparatus includes a noise estimator that estimates a noise pattern of a spectral image of a set of spectral images corresponding to different energy ranges, wherein the noise pattern is used to estimate local structure models for a voxel of the spectral image, a model fitter that fits a set of the local structure models to a three dimensional neighborhood of voxels in the image about a voxel in the image, and a model selector that selects one of the local structure models for the voxel based on the fittings and predetermined model selection criteria.

In another aspect, a method includes generating a calcium probability map based on a probabilistic decomposition of de-noised spectral images, enhancing the calcium probability map by performing a total variation functional minimization of the calcium probability map and generating a binary mask representing the bone and calcium segmentation based on the enhanced calcium probability map and a predetermined threshold.

In another aspect, a method includes generating one or more iodine distribution maps based on a vector decomposition of de-noised spectral images and estimating an iodine map based on the one or more iodine distribution maps and a binary mask representing the bone and calcium segmentation.

In another aspect, a method includes generating a virtual contrast enhanced intermediate image for every energy image of a set of spectral image corresponding to different energy ranges based on de-noised spectral images, decomposed de-noised spectral images, an iodine map and a contrast enhancement factor, and generating final virtual contrast enhanced images by incorporating a simulated partial volume effect with the intermediate virtual contrast enhanced images.

In another aspect, a method includes generating a virtual non-contrast intermediate image for every energy image of a set of spectral images corresponding to different energy ranges based on the de-noised spectral images, decomposed de-noised spectral images and an iodine map, and generating final virtual non-contrast images by incorporating a simulated partial volume effect with the intermediate virtual contrast enhanced images.

Still further aspects of the present invention will be appreciated to those of ordinary skill in the art upon reading and understanding the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
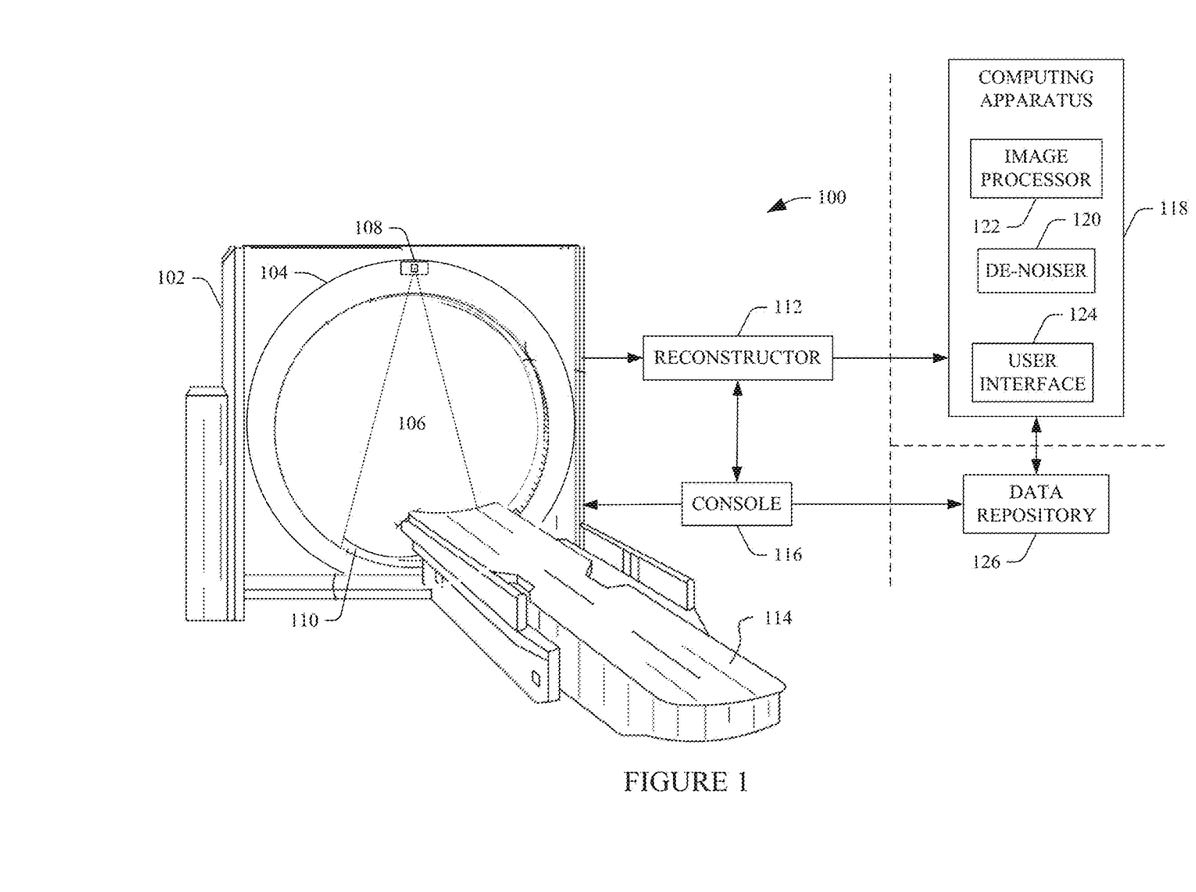
FIG. 1 schematically illustrates an imaging system in connection with a de-noiser and an image processor.

FIG. 1 illustrates an imaging system 100 such as a computed tomography (CT) scanner configured for spectral CT imaging. The imaging system 100 includes a stationary gantry 102 and a rotating gantry 104, which is rotatably supported by the stationary gantry 102. The rotating gantry 104 rotates around an examination region 106 about a longitudinal or z-axis.

The system 100 includes at least one radiation source 108, such as an x-ray tube, that is supported by the rotating gantry 104 and which rotates with the rotating gantry 104 about the examination region 106. The at least one radiation source 108 emits radiation that traverses the examination region 106. Where there are at least two radiation sources 108, each source can be configured to emit radiation having a different mean emission spectrum. Additionally or alternatively, one or more of the at least two sources 108 can be configured to controllably switch between at least two different emission voltages (kVp's) during scanning Multiple sources and/or kVp switching can be used for spectral CT acquisitions.

A radiation sensitive detector array 110 is located opposite the at least one radiation source 108, across the examination region 106. The radiation sensitive detector array 110 includes an array of detector pixels that detect radiation traversing the examination region 106 and generate projection data indicative thereof. The radiation sensitive detector array 110 can include conventional and/or energy-resolving detectors such as direct conversion detectors and/or a scintillator-based multi-spectral detector that includes at least two scintillators with different x-ray energy sensitivities respectively optically affixed to at least two photosensors with corresponding optical sensitivities (e.g., double decker or layer detector). The energy-resolving detectors can be used for spectral CT acquisitions.

A reconstructor 112 reconstructs the projection data and generates volumetric image data indicative of the examination region 106 and the portion of the object or subject therein. Where spectral data is acquired (e.g., where the projection data includes at least two measurements acquired concurrently and corresponding to different energy ranges via multiple sources, kVp switching and/or energy-resolving detectors), the reconstructor 112 can reconstruct individual spectral images for each of the different energy ranges and/or combination images based on the individual spectral images corresponding to two or more of the different energy ranges. The reconstructor 112 can also employ conventional non-spectral reconstruction algorithms.

A subject support 114, such as a couch, supports a subject (e.g., a human or animal) or object in the examination region 106 and can be used to position the subject with respect to x, y, and/or z axes and the examination 106 before, during and/or after scanning A general purpose computing system serves as an operator console 116, and includes an output device such as a display and an input device such as a keyboard, mouse, and/or the like. Software resident on the console 116 allows the operator to control the operation of the system 100, for example, allowing the operator to select a spectral imaging protocol, initiate scanning, etc.

A computing apparatus 118 includes one or more processors that execute one or more computer executable instructions embedded or encoded on computer readable storage medium such as physical memory. Additionally or alternatively, one or more of the computer executable instructions can be carried by a signal or carrier wave and executed by the one or more processors. In the illustrated embodiment, the computer executable instructions include instructions for implementing a de-noiser 120 and/or an image processor 122. In another embodiment, the de-noiser 120 and/or the image processor 122 are implemented via the console 116 and/or other device.

The de-noiser 120 is configured to de-noise spectral noise from reconstructed spectral images, removing or reducing spectral noise therefrom and producing de-noised reconstructed spectral images. As described in greater detail below, in one instance, the de-noiser 120 removes or reduces spectral noise while preserving the underlying spectral information and the object structure. In one instance, this allows radiation dose reduction for a given image quality. Alternatively, image quality can be enhanced for a given dose. Alternatively, a combination of dose reduction and image quality enhanced can be achieved. Additionally or alternatively, the de-noiser 120 can de-noise estimated monochromatic images, which can be simulated to estimate any keV image using an appropriate combination of photoelectric and Compton components.

An image processor 122 processes the de-noised reconstructed spectral images and/or the monochromatic images. As described in greater detail below, this includes one or more of performing a bone and/or calcium segmentation, creating an iodine map of a quantitative distribution of the iodine in a study, generating virtual contrast enhanced (VCE) images, and/or generating virtual non-contrast (VNC) images. Such bone and calcification segmentation can highly utilize the additional quantitative spectral information, be utilized within a beam hardening correction algorithm, be utilized with a monochromatic image reconstruction algorithm, etc. The iodine map provides an improved quantitative distribution of the iodine in the study.

Virtually enhancing contrast allows for reducing the amount of contrast material administered to a patient for a given image quality. Alternatively, it allows for saving a study where the scanning timing from administration has been missed and the resulting image has suboptimal image quality, which may result in a repeat scan and further contrast material. Alternatively, it allows a clinician to manually tweak image processing parameters via a mouse, keyboard or the like to probe images in real time and obtain a desired visualization result. The VNC image may eliminate the need for a non-contrast scan, which can decrease radiation exposure, save time, and prolong tube life.

The computing apparatus 118 also includes a user interface 124, which allows a user to interact with the computing apparatus 118. In one instance, this includes allowing a clinician to choose which of the above-noted image processing features (i.e., bone and calcium segmentation, iodine map generation, VNC image generation and/or VCE image generation) to employ for a given study. The user interface 124 also allows the clinician to set and/or change various image processing parameters. For example, the clinician can use the user interface 124 to change the amount of de-noising for the study. This can be done dynamically in real time with the results being presented in real time.

That is, the clinician, viewing results, can change a parameter that in response invokes the computing apparatus to process the de-noised reconstructed spectral images based on the changed parameter and visually present the results. Other parameters which may be user configurable include, but are not limited to, a contrast enhancement factor for VCE image processing, parameters affecting the aggressiveness of the simulate partial volume effect for VCE and VNC image generation, thresholds for selecting de-local structural models for de-noising, scaling factors for bone and calcium segmentation, weighting factors for fitting local structure models to voxels, etc.

A data repository 126 can be used to store the reconstructed images, de-noised reconstructed images and/or processed reconstructed images and/or de-noised reconstructed images and can be accessed by one or more of the console 116, the image processor 122, the de-noiser 120 and/or other device. The data repository 126 can be local to the system 100, remote from the system 100, distributed, etc. The data repository 126 may include a database, a server, a picture archiving and communication system (PACS), radiology information system (RIS), a hospital information system (HIS), an electronic medical record (EMR), and/or other electronic storage device or memory.

Figure 2:
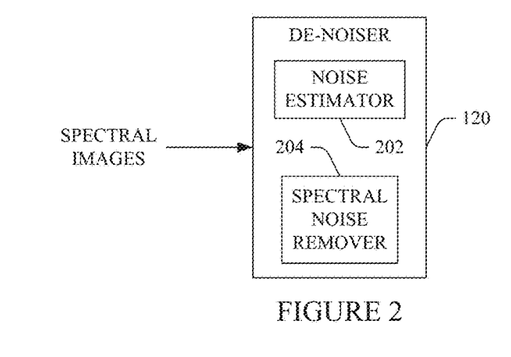
FIG. 2 schematically illustrates an example of the de-noiser.

FIG. 2 schematically illustrates an example of the de-noiser 120. Generally, in this embodiment, the de-noiser 120 is configured to determine a noise pattern for a spectral image in a set of spectral images corresponding to different energy ranges and reduce spectral noise of the spectral images based on the noise pattern. The illustrated de-noiser 120 receives as input a set of spectral images, which could include a set of reconstructed spectral images from the scanner 100, the repository 126 and/or elsewhere, and/or a set of estimated monochromatic images.

A noise estimator 202 estimates a local noise value of each voxel of a spectral image and generates a noise model or pattern for the spectral image based on the local noise values, and the noise model is used to estimate structures in the spectral image. The noise estimator 202 can use known and/or other approaches to estimate noise. Suitable approaches include, but are not limited to, a Monte Carlo estimate, an analytical approach such as the one discussed in Wunderlich and Noo, Phys. Med. Biol. 53 (2008), 2472-2493, an image based approach such as the one described in PCT patent application Ser. No. PCT/IB2009/054913, filed on Oct. 29, 2010, and entitled "ENHANCED IMAGE DATA/DOSE REDUCTION," which is incorporated by reference in its entirety herein, and/or other approach.

A spectral noise remover 204 removes spectral image noise from the spectral images based on the estimated noise model, generating de-noised spectral images, while preserving underlying spectral information and/or anatomical structure in the different energy images, thereby improving the signal to noise ratio of the spectral images. An example of this is described in connection with FIG. 3, where the spectral noise remover 204 includes a model fitter 302 that fits local structure models, which are determined based on the estimated noise pattern, to a three dimensional region or neighborhood of voxels about a voxel, for one or more of the voxels in the spectral image.

Figure 3:
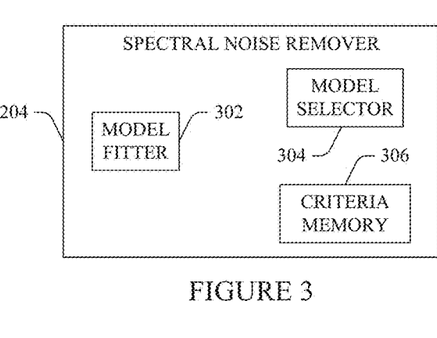
FIG. 3 schematically illustrates an example of a spectral noise remover of the de-noiser.

The spectral noise remover 204 also includes a model selector 304 that selects a local structure model for each voxel in an image based on predetermined selection criteria stored in criteria memory 306. Once a model is selected for each voxel, it is utilized by the spectral noise remover 204 to de-noise or remove the noise in the spectral images, where a new estimated value of a voxel is a value determined by the selected model and replaces the original value of the voxel. The resulting spectral images include de-noised spectral images, or image quality enhanced spectral image for the different energy ranges.

With reference to FIGS. 1, 2 and 3, an example noise removal approach for the de-noiser 120 follows. For this example, $v_{i,j,k}^{E_e}$ represents a voxel in the volume $V^{E_e}$, where the volume obtained by energy $E_e$. EQUATION 1 includes a least squares approach that can be used to fit the local structure models:

$$\hat{p}^{E_e} = \underset{p}{\mathrm{argmin}} \qquad \text{EQUATION 1}$$

-continued $$\sum_{i'=-n}^{n}\sum_{j'=-n}^{n}\sum_{k'=-n}^{n}\left(v_{i+i',j+j',k+k'}^{Ee} - M_{i',j',k'}^{m}(p)\right)^2 w_{i',j',k'}^2,$$

where $M_{i',j',k'}^{m}(p)$ is the model value for the (i+i',j+j',k+k') voxel in the volume and $w_{i',j',k'}$ are weight factors. The weight factors can be considered a localization kernel, which is a multiplication of two weight functions as shown in EQUATION 2:

$$w_{i',j',k'} = w_{i',j',k'}^{spatial} w_{i',j',k'}^{HU}, \quad \text{EQUATION 2}$$

where $w_{i',j',k'}^{spatial}$ represents weights to the neighbors according to their spatial distance to the voxel and $w_{i',j',k'}^{HU}$ represents weights to the neighbors according to their intensity-distance to the voxel in the Hounsfield Unit (HU) space.

The $w_{i',j',k'}^{spatial}$ function can be determined based on EQUATION 3:

$$w_{i',j',k'}^{spatial} = \sqrt{\exp\left(-\frac{((i'dx)^2 + (j'dx)^2 + (k'dz)^2)}{2\sigma_{spatial}^2}\right)}, \quad \text{EQUATION 3}$$

where dx is the size of the pixel in millimeters (mm), dz is the slice width in mm and $\sigma_{spatial}$ is an algorithm parameter that controls the aggressiveness of the weights.

The $w_{i',j',k'}^{Hu}$ function can be determined based on EQUATION 4:

$$w_{i',j',k'}^{HU} = \sqrt{\exp\left(-\sum_{e}\frac{\left(v_{i,j,k}^{Ee} - v_{i+i',j+j',k+k'}^{Ee}\right)^2}{2\left(\hat{n}_{i,j,k}^{Ee}m\right)^2}\right)} \quad \text{EQUATION 4}$$

where m is an algorithm parameter that controls the aggressiveness of the weights and $\hat{n}_{i,j,k}$ is the local noise level estimate of voxel $v_{i,j,k}$, which is estimated by the noise estimator 202 as described above.

Suitable models include, but are not limited to, a constant model (i.e., $M_{i',j',k'}(c)=c$) that models homogeneous regions and a second order polynomial that models the non-homogeneous regions (i.e., regions that includes curvatures). Other models can additionally or alternatively be used. The model selector 304 can use various known and/or other classifiers to select a suitable model. In this example, the illustrated model selector 304 utilizes INEQUALITY 1:

$$\text{Max}_{e} \frac{\text{local STD in } (i,j,k) \text{ over } \hat{V}_1^{Ee}}{\text{local STD in } (i,j,k) \text{ over } V^{Ee}} > \text{Threshold} \quad \text{INEQUALITY 1}$$

where $\hat{V}_1^{Ee}$ is the noiseless estimated voxel of the first model and threshold corresponds to criteria stored in criteria memory 306. In this example, if INEQUALITY 1 is satisfied, the noise removal is performed using the second model parameter.

Once a model is chosen, the spectral noise remover 204 uses the model to de-noise the spectral images, thereby generating de-noised spectral images. In one instance, the same noise model type and the same fitting weights are used for all the different energy images. This allows removal of noise while preserving consistent results in the spectral images across the different energy ranges. In another instance, different noise model types and/or the fitting weights are used for one or more of the different energy images.

Figure 4:
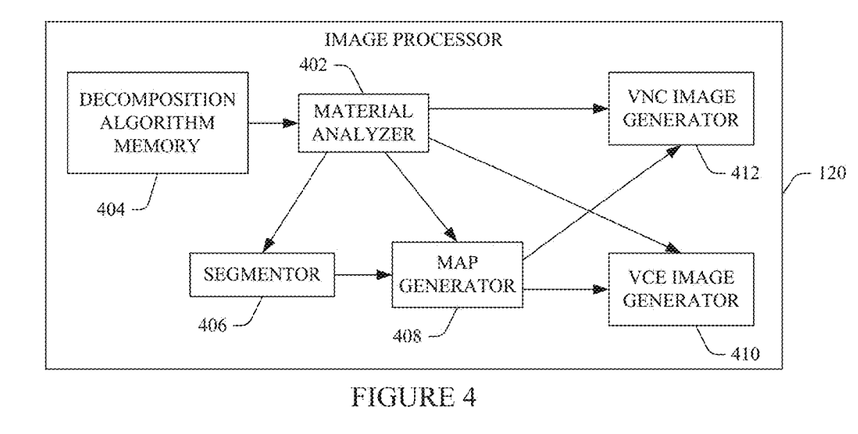
FIG. 4 schematically illustrates an example of the image processor.

FIG. 4 schematically illustrates an example of the image processor 120. In this embodiment, the image processor 120 includes a material analyzer 402, decomposition algorithm memory 404, a segmentor 406, a map generator 408, a virtual contrast enhanced (VCE) image generator 410, and a virtual non-contrast (VNC) image generator 412.

Figure 5:
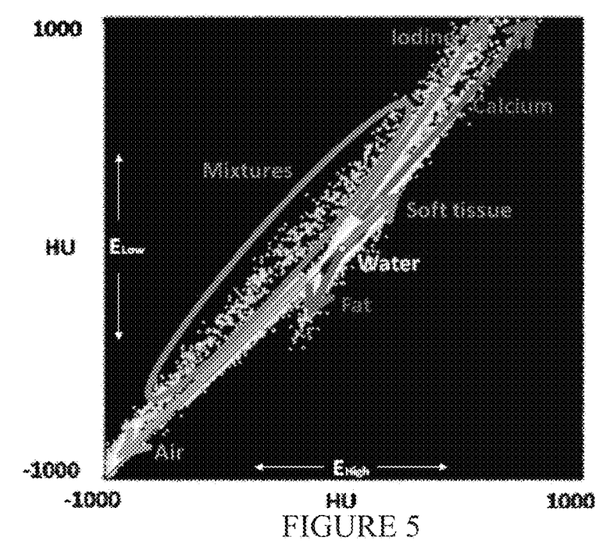
FIG. 5 shows an example of an energy map/energy scatter plot of a dual energy study and several of the material response vectors.

The material analyzer 402 decomposes the spectral images de-noised by the de-noiser 118 and/or other de-noised spectral images according to different material bases as each material has a unique attenuation spectral response, i.e., each material has a unique material response vector on an image-based energy map. A dual energy scanner is able to distinguish, in principal, between tissues or material of variable density with greater resolving power than a conventional CT scanner. This is shown in connection with FIG. 5 which shows an example of an energy map/energy scatter plot of a dual energy study and several of the material response vectors.

Figure 6:
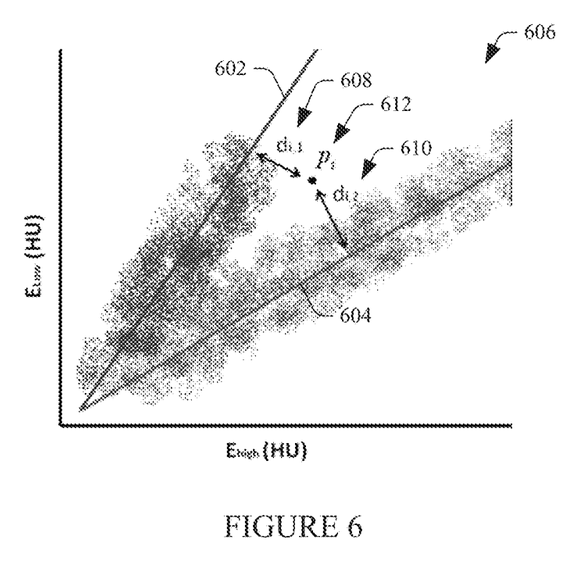
FIG. 6 shows two material response vectors in an energy map and the shorter distances from a measurement point to the two vectors.

The material analyzer 402 decomposes the de-noised reconstructed spectral images being analyzed based on various known and/or other decomposition algorithms such as one or more decomposition algorithms stored in the decomposition algorithm memory 404. Examples of non-limiting decomposition algorithms are further discussed next. One suitable decomposition algorithm is based on a vector decomposition approach. For example, the material analyzer 402 can estimate material distribution maps by solving the linear equations of EQUATION 5:

$$\sum_{m=1}^{n} \vec{M}_m \alpha_{i,j,k}^m = \begin{bmatrix} \hat{v}_{i,j,k}^1 \\ \vdots \\ \hat{v}_{i,j,k}^n \end{bmatrix} \quad \text{EQUATION 5}$$

where $\vec{M}_m$ is a material vector related to material m, $\hat{V}^e$ is the volume related to energy e obtained after de-noising via the de-noiser 118, n is the number of energy bins and $\alpha^m$ is an estimated material distribution map related to material m. Another suitable decomposition algorithm is based on a probabilistic decomposition approach. For example, the material analyzer 402 can estimate material distribution maps based of EQUATION 6:

$$\{\hat{\alpha_m}\} = \operatorname*{argmax}_{\{\alpha_m\},\Sigma_m\alpha_m=1} \sum_{i} \log \sum_{m=1}^{n} f(p_i \mid M_m)\alpha_m = \operatorname*{argmax}_{\{\alpha_m\},\Sigma_m\alpha_m=1} \sum_{i=1}^{n} \log \sum_{m=1}^{n} f(d_{i,m} \mid M_m)\alpha_m, \quad \text{EQUATION 6}$$

where $f(p_i|M_m)$ is the probability density function of a point $p_i$ to contain material $M_m$ and $d_{i,m}$ is the shortest distance in the energy map between point $p_i$ to the material vector related to material $M_m$. This can be seen in FIG. 6, which shows two material response vectors 602 and 604 in an energy map 606 and the shorter distances 608 and 610 from a measurements point $p_i$ 612 to the two vectors 602 and 604.

The material probability map estimate can be determined based of EQUATION 7:

$$P_m(v_i := M_m) = \frac{f(v_i \mid io)\alpha_m}{\sum_m f(v_i \mid io)\alpha_m},$$ EQUATION 7 where $P_m$ is the material probability map of material $M_m$. Generally, this approach uses the distribution of the distances in the energy map of the voxels to the material response vectors as a probability mixture model of several materials. The output of this decomposition includes material probability maps that represent the probability of each voxel including specific material.

Figure 7:
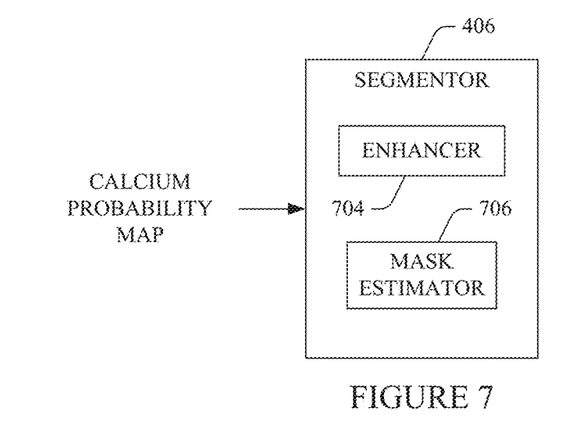
FIG. 7 schematically illustrates an example segmentor of the image processor.

Returning to FIG. 4 and with reference to FIG. 7, the segmentor 406 is configured to at least segment bone and calcifications based on decomposed de-noise spectral images.

As shown in FIG. 7, the segmentor 406 receives as input a calcium probability map $P_m$, which is estimated by the material analyzer 402 based on calcium, iodine and soft tissue and/or other materials, using the probabilistic material decomposition algorithm (EQUATIONS 6 and 7) from the memory 404.

An enhancer 704 enhances the probabilistic material decomposition using a total variation functional minimization or other approach. In this example, the enhancer 702 performs a total variation functional minimization based on EQUATION 8:

$$\hat{u} = \underset{u}{\text{Min}} \int\int\int_{i,\,j,\,k} |\nabla u| + \lambda \int\int\int_{i,\,j,\,k} (P_m(i,j,k) - u(i,j,k))^2 \, di\, dj\, dk,$$ EQUATION 8 where $\lambda$ is a positive parameter that controls the scale of the segmentation solution. The parameter $\lambda$ can be a default or user specified value. Various approaches can be used to solve EQUATION 8. A non-limiting approach can be found in Tony F. Chan, Jianhong Shen, Image Processing and Analysis, SIAM Books 2005.

The segmentor 406 further includes a mask estimator 704 that estimates an image binary map, which represents the segmentation of bone and calcification. In this example, the mask estimator 706 generates the map B based on EQUATION 9:

$$B = \hat{u} > \text{Threshold}.$$ EQUATION 1

As noted above, the resulting bone and calcification segmentation can highly utilize the additional quantitative spectral information, be utilized within a beam hardening correction algorithm, be utilized with a monochromatic image reconstruction algorithm, etc.

Figure 8:
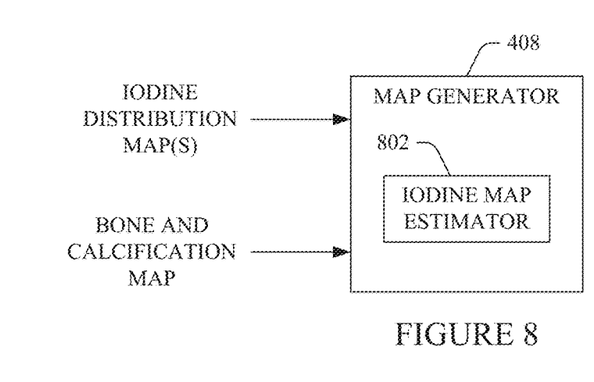
FIG. 8 schematically illustrates an example material map generator of the image processor.

Returning to FIG. 4 and with reference to FIG. 8, the illustrated map generator 408 is configured to generate an iodine map. Generally, the map generator 408 is configured to estimate an iodine map based on decomposed de-noised spectral images and the bone and calcium mask. For this example, the iodine map incorporates calcium, fat, soft tissue, and iodine. In other embodiments, more, less and/or different materials can be used.

As shown in FIG. 8, the map generator 408 receives as input iodine distribution maps generated based on the vector decomposition (EQUATION 5) of the material analyzer 402 and the bone and calcification map from the segmentor 406. In this dual energy example, the map generator 408 receives a first iodine distribution map, $\alpha_{Soft}^{Iodine}$, based on iodine and soft tissue and a second iodine distribution map $\alpha_{Fat}^{Iodine}$, based on iodine and fat. In instances with three or more different energy ranges, a single iodine map for iodine, soft tissue and fat can be generated and/or more iodine maps can be generated.

An iodine map estimator 802 estimates an iodine map, IM, based on EQUATION 10:

EQUATION 10

$$IM(i,j,k) = \begin{cases} 0, & B(i,j,k) \\ \alpha_{Fat}^{Iodine}(i,j,k)q, & |\alpha_{Fat}^{Iodine}(i,j,k)| < |\alpha_{Soft}^{Iodine}(i,j,k)| \wedge \hat{v}_{i,j,k}^e < 0 \forall e \,, \\ \alpha_{Soft}^{Iodine}(i,j,k)q, & \text{Otherwise} \end{cases}$$

where q is a constant scale factor that is dependent on the required quantitative unit. As noted above, the resulting iodine map IM provides an improved quantitative distribution of the iodine in the study.

Figure 9:
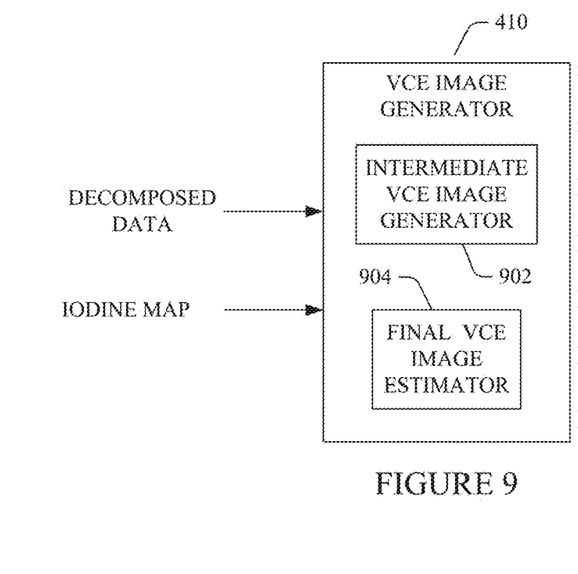
FIG. 9 schematically illustrates an example virtual contrast enhanced image generator of the image processor.

Returning to FIG. 4 and with reference to FIG. 9, the illustrated VCE image generator 410 is configured to compensate for a reduction of contrast material by virtual enhancement of the spectral images. The VCE image generator 410 receives as input the de-noised spectral images, the decomposed de-noise spectral images, and the iodine map generated by the map generator 408.

An intermediate VCE 902 generates, for every energy, e, a preliminary VCE image based on EQUATION 11:

$$vt_{i,j,k}^{E_e} = v_{i,j,k}^{E_e} + \gamma \frac{\vec{M}_{Iodine}(e)}{\|\vec{M}_{Iodine}\|} IM_{i,j,k},$$ EQUATION 11 where $\gamma$ is the enhancement factor. In one instance, $\gamma = 1/x - 1$ in order to compensate for a contrast material volume reduction by factor of x. In other instances, $\gamma$ can be a different value such as a default or user specified value. A final VCE image estimator 904 estimates a final image based on the intermediate image and a simulated partial volume effect based on EQUATION 12:

$$vce_{i,j,k}^{E_e} = \frac{|\nabla v_{i,j,k}^{E_e}|\beta + \delta}{|\nabla vt_{i,j,k}^{E_e}|\beta + \delta} vt_{i,j,k}^{E_e} + \left(1 - \frac{|\nabla v_{i,j,k}^{E_e}|\beta + \delta}{|\nabla vt_{i,j,k}^{E_e}|\beta + \delta}\right) LPF\!\left(vt_{i,j,k}^{E_e}\right).$$ EQUATION 12 where LPF is a low pass filter over the image and $\beta$ and $\delta$ are parameters that control an aggressiveness of the simulated partial volume effect.

As noted above, virtually enhancing contrast allows for reducing the amount of contrast material administered to a patient for a given image quality. Alternatively, it allows for saving a study where the scanning timing from administration has been missed and the resulting image has suboptimal image quality, which may result in a repeat scan and further contrast material. Alternatively, it allows a clinician to manually tweak image processing parameters via a mouse, keyboard or the like to probe images in real time and obtain a desired visualization result.

Figure 10:
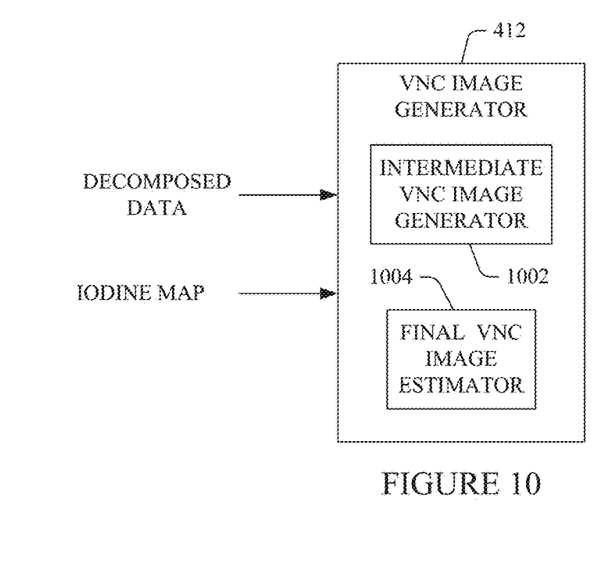
FIG. 10 schematically illustrates an example virtual non-contrast image generator of the image processor.

Returning to FIG. 4 and with reference to FIG. 10, the VNC image generator 412 is configured to estimate VNC images. The VNC image generator 412 receives as input the decomposed data generated by the material analyzer 402 and the iodine map IM generated by the map generator 408.

An intermediate VNC image generator 1002 generates, for every energy, e, a preliminary VNC image as follow based on EQUATION 13:

$$vp_{i,j,k}^{E_e} = v_{i,j,k}^{E_e} - \frac{\vec{M}_{Iodine}(e)}{\|\vec{M}_{Iodine}\|} IM_{i,j,k}. \qquad \text{EQUATION 13}$$

A final VNC image estimator 1004 estimates a final image based on the intermediate image and the simulated partial volume effect based on EQUATION 14:

$$vnc_{i,j,k}^{E_e} = \qquad \text{EQUATION 14}$$
$$\frac{|\nabla v_{i,j,k}^{E_e}|\beta + \delta}{|\nabla vp_{i,j,k}^{E_e}|\beta + \delta} vp_{i,j,k}^{E_e} + \left(1 - \frac{|\nabla v_{i,j,k}^{E_e}|\beta + \delta}{|\nabla vp_{i,j,k}^{E_e}|\beta + \delta}\right) LPF(vp_{i,j,k}^{E_e}).$$

where LPF is a low pass filter over the image and β and δ are parameters that control the aggressiveness of the simulated partial volume effect. The VNC image may eliminate the need for a non-contrast scan, which can decrease radiation exposure, save time, and prolong tube life.

FIGS. 11, 12, 13, 14 and 15 illustrate various methods for processing a set of reconstructed spectral CT images and/or a set of estimated monochromatic images.

It is to be appreciated that the ordering of the below acts is for explanatory purposes and not limiting. As such, other orderings are also contemplated herein. In addition, one or more of the acts may be omitted and/or one or more other acts may be included.

Figure 11:
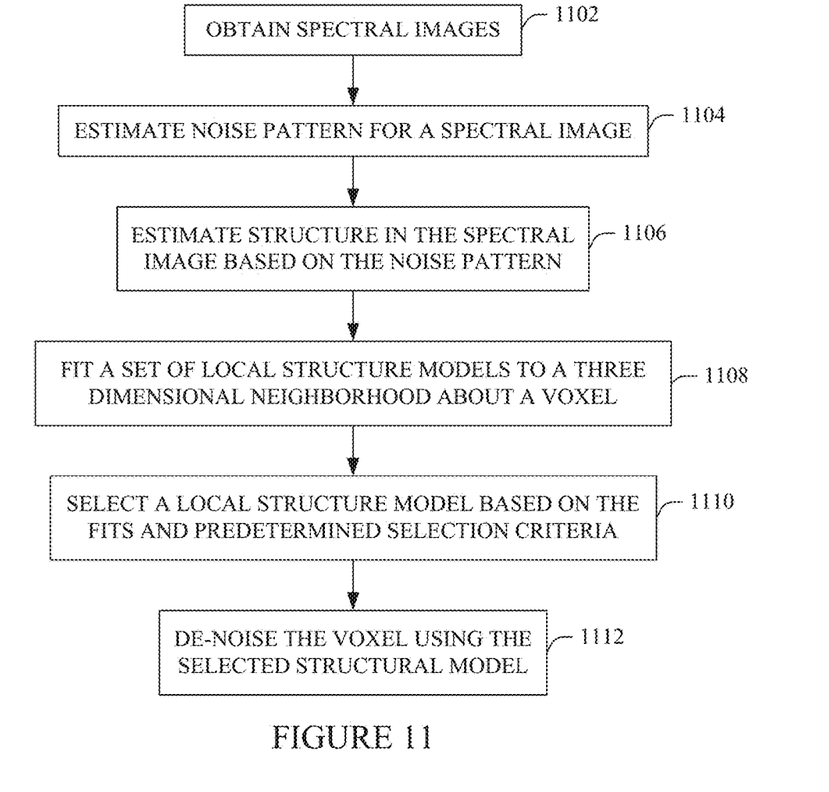
FIG. 11 illustrates an example method for de-noising spectral images.

Initially referring to FIG. 11, an example method for de-noising the spectral images is illustrated.

At 1102, a set of spectral images are obtained.

At 1104, a noise model is estimated for a spectral image of the set of spectral images.

At 1106, structures in the image are estimated based on the noise model, producing local structure models.

At 1108, a set of the local structure models corresponding to a voxel in the image are fitted to a three dimensional neighborhood of voxels about the voxel.

At 1110, a structure model from the set of local structure models is selected for the voxel based on the fits and predetermined selection criteria.

At 1112, the voxel is de-noised based on the selected model, wherein a value of the voxel is replaced with a value determined by the selected model.

The above can be repeated for one or more other voxels of one or more of the other spectral images, producing de-noised spectral images for the different energy ranges.

Figure 12:
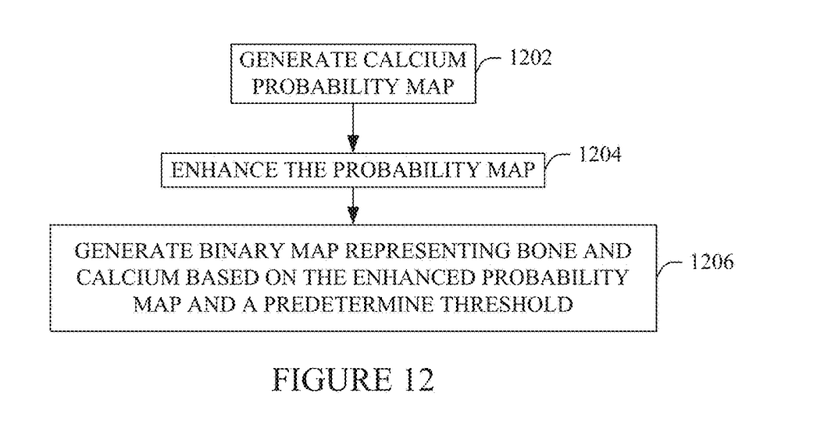
FIG. 12 illustrates an example method for determining bone and calcium segmentation binary mask for de-noised spectral images.

Turning to FIG. 12, an example method for generating a bone and calcium segmentation for the spectral images is illustrated.

At 1202, a calcium probability map is generated based on a probabilistic decomposition of the de-noised spectral images.

At 1204, the calcium probability map is enhanced by performing a total variation functional variation minimization of the calcium probability map.

At 1206, a binary map representing the bone and calcium segmentation is determined based on the enhanced calcium probability map and a predetermined threshold.

Figure 13:
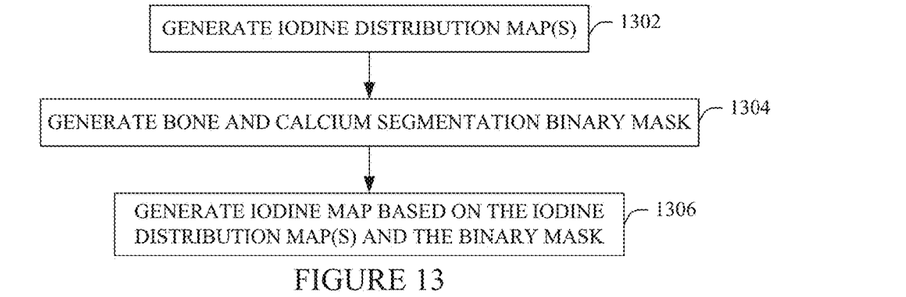
FIG. 13 illustrates an example method for determining an iodine map for de-noised spectral images.

Next, FIG. 13 illustrates an example method for generating an iodine map for the spectral images.

At 1302, one or more iodine distribution maps are generated based on a vector decomposition of the de-noised spectral images.

At 1304, a bone and calcium segmentation binary mask is generated, for example, as described in connection with FIG. 12.

At 1306, an iodine map is estimated based on the iodine distribution maps and the bone and calcium segmentation binary mask.

Figure 14:
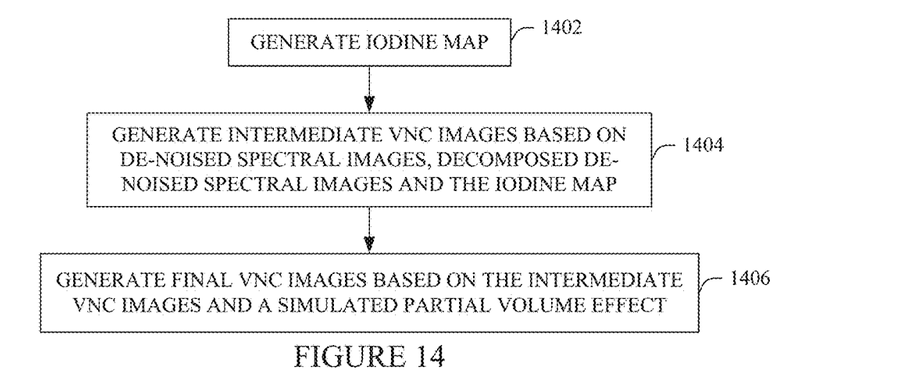
FIG. 14 illustrates an example method for determining virtual non contrast images based on de-noised spectral images.

In FIG. 14, an example method for generating virtual non-contrast (VNC) images for the spectral images is illustrated.

At 1402, an iodine map is estimated, for example, as described in connection with FIG. 13.

At 1404, intermediate VNC images are estimated for every energy based on the de-noised images, vector decomposed de-noised images, and the iodine map.

At 1406, final VNC images are generated by incorporating a simulated partial volume effect with the intermediate VNC images.

Figure 15:
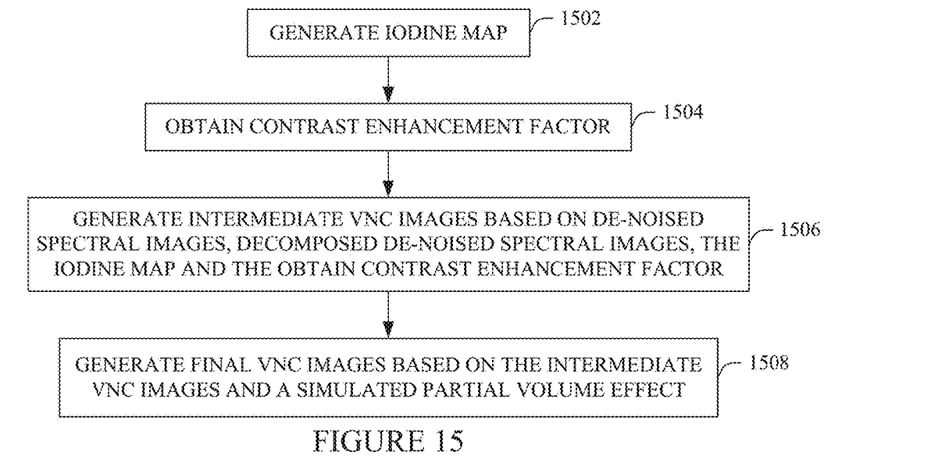
FIG. 15 illustrates an example method for determining virtual contrast enhanced images based on de-noised spectral images.

FIG. 15 illustrates an example method for generating virtual contrast enhanced (VCE) images for the spectral images is illustrated.

At 1502, an iodine map is estimated, for example, as described in connection with FIG. 13.

At 1504, a contrast enhancement factor is obtained.

At 1506, intermediate VCE images are estimated for every energy based on the de-noised images, vector decomposed de-noised images, the iodine map, and the contrast enhancement factor.

At 1508, final VCE images are generated by incorporating a simulated partial volume effect with the intermediate VCE images.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   decomposing de-noised spectral images into one or more material components, wherein decomposing comprises generating a calcium probability map based on a probabilistic decomposition of de-noised spectral images;
   enhancing the calcium probability map by performing a total variation functional variation minimization of the calcium probability map; and
   generating a binary mask based on the enhanced calcium probability map and a predetermined threshold.

2. The method of claim 1, wherein the binary mask represents segmented bone and calcium.

3. The method of claim 1, wherein decomposing comprises generating one or more iodine distribution maps based on a vector decomposition of the de-noised spectral images; and further comprising:
   estimating an iodine map based on the one or more iodine distribution maps and the binary mask.

4. The method of claim 3, wherein the iodine map represents a quantitative distribution of iodine.

5. The method of claim 3, wherein the one or more iodine distribution maps each include iodine and another material.

6. The method of claim 5, wherein the other material includes fat or soft tissue.

7. The method of claim 3, further comprising:
   generating a virtual non-contrast intermediate image for each energy image of a set of spectral images corresponding to different energy ranges based on the de-noised spectral images, the decomposed de-noised spectral images, and the iodine map; and
   generating final virtual non-contrast images by incorporating a simulated partial volume effect with the virtual non-contrast intermediate images.

8. The method of claim 3, comprising:
   generating a virtual contrast enhanced intermediate image for each energy image of a set of spectral image corresponding to different energy ranges based on the de-noised spectral images, the decomposed de-noised spectral images, the iodine map, and a contrast enhancement factor; and
   generating final virtual contrast enhanced images by incorporating a simulated partial volume effect with the intermediate virtual contrast enhanced images.

9. A non-transitory storage medium, comprising one or more computer readable instructions which cause one or more processors to:
   decompose de-noised spectral images into one or more material components, which includes generating a calcium probability map based on a probabilistic decomposition of de-noised spectral images;
   enhance the calcium probability map by performing a total variation functional variation minimization of the calcium probability map; and
   generate a binary mask based on the enhanced calcium probability map and a predetermined threshold.

10. The non-transitory storage medium of claim 9, wherein the one or more computer readable instructions cause one or more processors to:
    generate one or more iodine distribution maps based on a vector decomposition of the de-noised spectral images; and
    estimate an iodine map based on the one or more iodine distribution maps and the binary mask.

11. The non-transitory storage medium of claim 10, wherein the one or more computer readable instructions cause one or more processors to:
    generate a virtual non-contrast intermediate image for each energy image of a set of spectral images corresponding to different energy ranges based on the de-noised spectral images, the decomposed de-noised spectral images, and the iodine map; and
    generate final virtual non-contrast images by incorporating a simulated partial volume effect with the virtual non-contrast intermediate images.

12. The non-transitory storage medium of claim 10, wherein the one or more computer readable instructions cause one or more processors to:
    generate a virtual contrast enhanced intermediate image for each energy image of a set of spectral image corresponding to different energy ranges based on the de-noised spectral images, the decomposed de-noised spectral images, the iodine map, and a contrast enhancement factor; and
    generate final virtual contrast enhanced images by incorporating a simulated partial volume effect with the intermediate virtual contrast enhanced images.

13. A system, comprising:
    an image processor configured to decompose de-noised spectral images into one or more material components;
    generate a calcium probability map based on a probabilistic decomposition of de-noised spectral images;
    enhance the calcium probability map by performing a total variation functional variation minimization of the calcium probability map; and
    generate a binary mask based on the enhanced calcium probability map and a predetermined threshold.

14. The system according to claim 13, wherein the image processor is further configured to:
    generate one or more iodine distribution maps based on a vector decomposition of the de-noised spectral images; and
    estimate an iodine map based on the one or more iodine distribution maps and the binary mask.

15. The system according to claim 13, wherein the image processor is further configured to:
    generate a virtual non-contrast intermediate image for each energy image of a set of spectral images corresponding to different energy ranges based on the de-noised spectral images, the decomposed de-noised spectral images, and the iodine map; and
    generate final virtual non-contrast images by incorporating a simulated partial volume effect with the virtual non-contrast intermediate images.

16. The system according to claim 13, wherein the binary mask represents segmented bone and calcium.

17. The system according to claim 13, wherein decomposing comprises generating one or more iodine distribution maps based on a vector decomposition of the de-noised spectral images; and wherein the image processor is further configured to:
    estimate an iodine map based on the one or more iodine distribution maps and the binary mask.

18. The system according to claim 17, wherein the iodine map represents a quantitative distribution of iodine.

19. The system according to claim 17, wherein the one or more iodine distribution maps each include iodine and another material.

20. The system according to claim 17, wherein the image processor is further configured to:
    generate a virtual contrast enhanced intermediate image for each energy image of a set of spectral image corresponding to different energy ranges based on the de-noised spectral images, the decomposed de-noised spectral images, the iodine map, and a contrast enhancement factor; and
    generate final virtual contrast enhanced images by incorporating a simulated partial volume effect with the intermediate virtual contrast enhanced images.

* * * * *